United States Patent [19]

Wriede et al.

[11] Patent Number: 5,043,454
[45] Date of Patent: Aug. 27, 1991

[54] CROP PROTECTION AGENTS BASED ON 1-ARYL- OR 1-HETARYLIMIDAZOLECARBOXYLIC ESTERS

[75] Inventors: Ulrich Wriede, Mutterstadt; Gerhard Hamprecht, Weinheim; Hermann Koehler, Bobenheim; Bruno Wuerzer, Otterstadt, all of Fed. Rep. of Germany

[73] Assignee: BASF Aktiengesellschaft, Ludwigshafen, Fed. Rep. of Germany

[21] Appl. No.: 462,631

[22] Filed: Jan. 9, 1990

[51] Int. Cl.$^5$ ............... C07D 401/04; C07D 403/04; C07D 405/04; C07D 409/04; C07D 233/56; C07D 233/64; C07D 233/66

[52] U.S. Cl. .................... 548/337; 546/278; 544/238; 544/298; 544/300; 544/310; 544/316; 544/317; 544/319; 544/320; 544/321; 544/322; 544/324; 544/328; 544/331; 544/333; 544/405; 548/336; 548/343; 548/234; 548/235; 548/236; 548/225; 548/226; 548/227; 548/228; 548/229; 548/230; 548/232; 548/233; 548/182; 548/183; 548/184; 548/190; 548/191; 548/194; 548/213; 548/214; 548/243; 548/244; 548/245; 548/246; 548/247; 548/248

[58] Field of Search .............. 548/337, 343, 336, 234, 548/225, 228, 232, 183, 191, 214, 245, 248; 546/278; 544/238, 310, 319, 322, 331

[56] References Cited

U.S. PATENT DOCUMENTS

| | | | |
|---|---|---|---|
| 4,578,106 | 3/1986 | Leone-Bay et al. | 548/337 |
| 4,591,377 | 5/1986 | Leone-Bay et al. | 71/92 |
| 4,595,400 | 6/1986 | Leone-Bay et al. | 71/92 |
| 4,639,266 | 1/1987 | Heubach et al. | 71/92 |
| 4,711,962 | 12/1987 | Leone-Bay | 548/337 |
| 4,755,213 | 7/1988 | Schmierer et al. | 71/92 |
| 4,808,213 | 2/1989 | Schmierer et al. | 71/92 |

FOREIGN PATENT DOCUMENTS 1218662  3/1987  Canada .

Primary Examiner—John M. Ford
Attorney, Agent, or Firm—Keil & Weinkauf

[57] ABSTRACT

1-Aryl- and 1-hetarylimidazolecarboxylic esters of the general formulae Ia and Ib

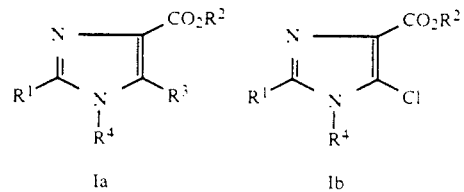

where
R$^1$ is halogen or substituted or unsubstituted C$_1$–C$_4$-alkyl;
R$^2$ is substituted or unsubstituted C$_1$–C$_6$-alkyl; C$_3$–C$_6$-alkenyl, C$_3$–C$_6$-alkynyl or C$_3$–C$_6$-cycloalkyl;
R$^3$ is hydrogen or C$_1$–C$_4$-alkyl;
R$^4$ is substituted or unsubstituted phenyl or 5- or 6-membered heteroaromatic, processes for their manufacture, and agents containing them.

2 Claims, No Drawings

1

CROP PROTECTION AGENTS BASED ON 1-ARYL- OR 1-HETARYLIMIDAZOLECARBOXYLIC ESTERS

The present invention relates to 1-aryl- and 1-hetarylimidazolecarboxylic esters of the general formulae Ia and Ib $$\underset{\text{Ia}}{\underset{R^4}{\overset{N}{\underset{\parallel}{\bigvee}}}\overset{CO_2R^2}{\underset{R^3}{\bigvee}}} \qquad \underset{\text{Ib}}{\underset{R^4}{\underset{\parallel}{\overset{N}{\underset{\parallel}{\bigvee}}}}\overset{CO_2R^2}{\underset{Cl}{\bigvee}}}$$

where $R^1$ is halogen or $C_1$–$C_4$-alkyl which may carry from one to three chlorine atoms, $R^2$ is $C_1$–$C_6$-alkyl which may carry from one to three of the radicals halogen, $C_1$–$C_4$-alkoxy and/or $C_1$–$C_4$-alkoxy-$C_1$–$C_4$-alkoxy, or is $C_3$–$C_6$-alkenyl, $C_3$–$C_6$-alkynyl or $C_3$–$C_6$-cycloalkyl, $R^3$ is hydrogen or $C_1$–$C_4$-alkyl and $R^4$ is a phenyl ring or a 5-membered or 6-membered heteroaromatic containing as heteroatoms one or two nitrogen atoms and/or an oxygen or a sulfur atom in the ring, and these aromatic rings may carry from one to three of the following groups: halogen, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfinyl, $C_1$–$C_4$-alkylsulfonyl, $C_1$–$C_4$-alkylcarbonyl, $C_1$–$C_4$-alkoxycarbonyl, carboxyl, nitro and/or cyano.

The present invention furthermore relates to a process for the preparation of the compounds Ia and Ib and herbicides which contain the 2-(4-hetaryloxy)- or 2-(4-aryloxy)-phenoxyacetic or -propionic acid derivatives and/or cyclohexenone derivatives as herbicidal active ingredients and aryl- or hetarylimidazolecarboxylic acid derivatives as antidotes, and methods for selectively controlling undesirable plant growth with these herbicides.

EP-A 174 562 discloses 1-aryltriazolecarboxylic acid derivatives having crop-protecting activity. 1-Arylimidazolecarboxylic esters having growth-regulating properties (EP-A 243 615, EP-A 264 577) and 2-haloimidazolecarboxylic esters having a herbicidal action are also described (EP-A 127 446; EP-A 180 787; U.S. Pat. Nos. 4,711,962; 4,591,377 and 4,578,106).

Herbicidal active ingredients from the group consisting of the 2-(4-hetaryloxy)- or 2-(4-aryloxy)phenoxyacetic acid derivatives of the formula IV $$R^a\text{—}O\text{—}\underset{}{\underset{}{\bigcirc}}\text{—}O\text{—}\overset{R^c}{\underset{}{CH}}\text{—}CO_2R^b \qquad IV$$

where $R^a$ is phenyl, pyridyl, benzoxazyl, benzothiazyl or benzopyrazinyl, and these aromatic ring systems may carry up to two of the following radicals: halogen, $C_1$–$C_4$-alkyl, $C_1$–$C_4$-haloalkyl and/or $C_1$–$C_4$-halophenoxy, $R^b$ is hydrogen, $C_1$–$C_5$-alkyl, $C_3$–$C_5$-alkylideneimino, $C_3$–$C_5$-alkylideneiminooxy-$C_2$- or -$C_3$-alkyl or one equivalent of a plant-tolerated cation and $R^c$ is hydrogen or methyl, are used for controlling undesirable plants from the family of the gramineae (for example DE-A 22 23 894, DE-A 24 33 067, DE-A 25 76 251, DE-A 30 04 770, BE-A 868 875 and BE-A 858 618). However, the toleration of these substances by crops varies from commercially acceptable to non-tolerated, depending on the substituents and application rate.

The same situation is encountered with the cyclohexenone derivatives of the formula V $$\underset{R^h}{\underset{R^g}{\underset{R^f}{\bigvee}}}\overset{OR^i}{\underset{O}{\bigvee}}\overset{NOR^e}{\underset{R^d}{}} \qquad V$$

where $R^d$ is $C_1$–$C_4$-alkyl, $R^e$ is $C_1$–$C_4$-alkyl; $C_3$- or $C_4$-alkenyl, $C_3$- or $C_4$-alkynyl, $C_3$- or $C_4$-haloalkenyl or thenyl which may carry a halogen atom;

$R^f$ is $C_1$–$C_4$-alkyl which may be monosubstituted by $C_1$–$C_4$-alkylthio or $C_1$–$C_4$-alkoxy;

a 5-membered or 6-membered saturated or monounsaturated ring system which may contain, in addition to carbon members, an oxygen or sulfur atom or a sulfoxyl or sulfonyl group, and this ring may carry up to three of the following radicals: hydroxyl, halogen, $C_1$–$C_4$-alkyl, $C_1$–$C_4$-haloalkyl, $C_1$–$C_4$-alkoxy and/or $C_1$–$C_4$-alkylthio;

a 10-membered saturated or monounsaturated heterocyclic structure which contains two oxygen atoms or sulfur atoms and may be subtituted by up to three $C_1$–$C_4$-alkyl groups and/or methoxy groups;

phenyl, pyridyl or isoxazolyl, where these groups may carry up to three of the following radicals: $C_1$–$C_4$-alkyl, $C_1$–$C_4$-haloalkyl, $C_1$–$C_4$-alkoxy, $C_1$–$C_4$-alkylthio, $C_3$–$C_6$-alkenyloxy, $C_3$–$C_6$-alkynyloxy, $C_1$–$C_4$-alkoxy-$C_1$–$C_3$-alkyl, $C_1$–$C_4$-dialkoxy-$C_1$–$C_3$-alkyl, formyl, halogen and/or benzoylamino;

$R^g$ is hydrogen or hydroxyl or, when $R^f$ is $C_1$–$C_6$-alkyl, is $C_1$–$C_6$-alkyl;

$R^h$ is hydrogen, cyano, halogen or $C_1$–$C_4$-alkoxycarbonyl and $R^i$ is hydrogen or one equivalent of an environmentally compatible cation.

They are also described in the literature as herbicides (e.g. EP-A 228 598, EP-A 230 235, EP-A 238 021, U.S. Pat. No. 4,432,786, DE-A 24 39 104) and serve predominantly for controlling undesirable grasses in dicotyledon crops and in grasses which do not belong to the gramineae family. Depending on the structure of the substituents and the dose used, compounds from this group can also be employed for selectively controlling undesirable grasses in gramineous crops, such as wheat and rice.

It is an object of the present invention to provide compounds which overcome or greatly reduce the disadvantages encountered when using the abovementioned herbicides of the formulae IV and V. Such compounds are also referred to as antidotes or safeners.

We have found that this object is achieved by the 1-aryl- and 1-hetarylimidazonecarboxylic esters Ia and Ib defined at the outset. We have furthermore found processes for the preparation of these compounds Ia and Ib and methods for using these compounds together with the herbicides IV and V for influencing undesirable plant growth. The present invention furthermore relates to agents which contain the compounds Ia and Ib and/or herbicides of type IV or V, it being immaterial whether the herbicidal active ingredient and the antidote are formulated and applied together or separately or, if they are applied seperately, which is applied first.

The novel compounds of the formulae Ia and Ib are obtainable by various methods.

Thus, the compounds Ia are obtained, for example, by reacting an imidazolecarboxylic ester of the formula II with an aryl or hetaryl derivative III in a conventional manner in an inert organic solvent in the presence of a base to give Ia.

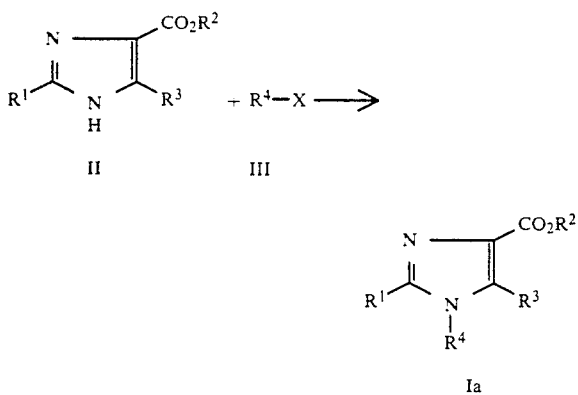

In formula III, X is halogen, such as fluorine, chlorine or bromine, preferably fluorine or chlorine.

The reaction can be carried out continuously or batchwise, under atmospheric pressure or pressures up to 30, preferably from 1 to 10, bar and at from 20° C. to 200° C., preferably from 50° C. to 170° C.

Examples of suitable solvents are n-hexane, decalin, toluene, xylene, chlorobenzene, tetrahydrofuran, dioxane, dimethylformamide, diethylformamide, dimethyl sulfoxide, acetone and ethanol. Toluene and dimethylformamide are preferred.

Suitable bases are sodium bicarbonate, sodium carbonate, potassium carbonate, sodium hydroxide, potassium hydroxide, sodium hydride, sodium methylate, sodium ethylate, potassium tert-butylate, triethylamine, diisopropylethylamine, N,N-dimethylaniline, pyridine, isoquinoline, N-methylpyrrolidine, N,N,N',N'-tetramethylethylenediamine and 1,8-diazabicyclo[5.4.0]undec-7-ene. However, sodium hydride, sodium methylate and triethylamine are preferred bases.

The preparation of the imidazolecarboxylic esters required for this purpose is described in, inter alia, ES-A 512 649 and EP-A 127 446.

The compounds Ib can be prepared from aryl- or hetarylimidazolecarboxylic esters Ia, in which $R^3$ is hydrogen, in a conventional manner by reaction with a chlorinating agent.

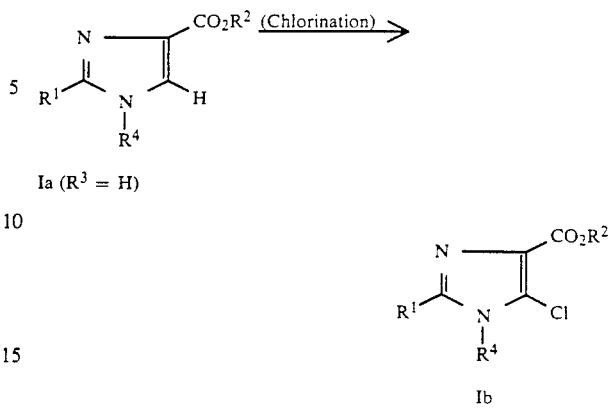

Examples of suitable chlorinating agents are phosphorus oxytrichloride, sulfuryl chloride, thionyl chloride, phosgene, phosphorus pentachloride, phosphorus trichloride and sulfur tetrachloride, sulfuryl chloride being preferred.

The reaction is usually carried out in the presence or absence of an inert organic solvent, such as chlorobenzene or dichlorobenzene, continuously or batchwise at from 20° C. to 200° C., preferably from 80° C. to 150° C., under atmospheric or slightly superatmospheric pressure (1-5 bar).

If the reaction is carried out in the presence of one of the abovementioned solvents, it is advisable also to use a free radical initiator, such as dibenzoyl peroxide or azobisisobutyronitrile, to accelerate the reaction.

In view of the intended use of the compounds Ia and Ib as crop protection agents, suitable substituents are the following radicals:

$R^1$ is alkyl, such as methyl, ethyl, propyl, isopropyl, n-butyl, sec-butyl, isobutyl or tert-butyl, preferably methyl or ethyl;

haloalkyl, such as chloromethyl, dichloromethyl, trichloromethyl, 1,1-dichloroethyl or 1-chloroethyl, preferably chloromethyl, dichloromethyl or trichloromethyl; halogen, such as fluorine, chlorine, bromine or iodine, preferably chlorine or bromine;

$R^2$ is alkyl as stated under $R^1$, and n-pentyl, 2-methylbutyl, 3-methylbutyl, 2,2-dimethylpropyl, n-hexyl, 2-methylpentyl, 3-methylpentyl, 4-methylpentyl, 2,2-dimethylbutyl, 3,3-dimethylbutyl, 2,3-dimethylbutyl or 2-ethylbutyl, preferably methyl or ethyl;

alkenyl, such as allyl, 2-butenyl, 3-butenyl, 1-methyl2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1,2-dimethyl-2-propenyl, 1,1-dimethyl-2-propenyl, 1-methyl-3-butenyl, 1-ethyl-2-propenyl, 2-hexenyl, 1-methyl-2-pentenyl, 1-ethyl-2-butenyl and 2-ethyl-2-butenyl, preferably allyl, 2-butenyl or 1-methyl-2-propenyl;

alkynyl, such as 2-propynyl, 2-butynyl, 3-butynyl, 1-methyl-2-propynyl, 1-methyl-2-butynyl, 1-ethyl-2-propynyl, 2-pentynyl, 3-pentynyl, 4-pentynyl or 1-methyl-2-pentynyl, preferably 2-propynyl, 1-methyl-2-propynyl or 2-butynyl;

cycloalkyl, such as cyclopropane, cyclobutane, cyclopentane or cyclohexane, preferably cyclopropane, cyclopentane or cyclohexane;

haloalkyl as stated under $R^1$, and fluoromethyl, difluoromethyl, trifluoromethyl, 2-fluoroethyl, 2,2-difluoroethyl or 2,2,2-trifluoroethyl, preferably difluoromethyl, trifluoromethyl, chloromethyl, dichloromethyl, trichloromethyl or 2-chloroethyl;

alkoxyalkyl, such as 2-methoxyethyl, 2-ethoxyethyl, 2-propoxyethyl, 3-methoxypropyl or 3-ethoxypropyl, preferably methoxyethyl or 2-ethoxyethyl;

alkoxyalkoxyalkyl, such as 2-methoxymethoxyethyl, 2-ethoxymethoxyethyl or 2-ethoxyethoxyethyl;

$R^3$ is hydrogen or alkyl as stated under $R^1$, preferably hydrogen, methyl or ethyl;

$R^4$ is a phenyl ring or a 5-membered or 6-membered heteroaromatic, such as pyrrole, pyrazole, imidazole, furan, thiophene, oxazole, thiazole, isoxazole, isothiazole, pyridine, pyridazine, pyrimidine or pyrazine, preferably pyridine or pyrimidine.

Preferred substituents of $R^4$ are alkyl as stated under $R^1$, in particular methyl, ethyl or isopropyl;

haloalkyl as stated under $R^2$, in particular trifluoromethyl or difluoromethyl;

alkoxy, such as methoxy, ethoxy, propoxy, 1-methylethoxy, butoxy, 1-methoxy, 2-methoxy or 1,1-dimethylethoxy, in particular methoxy, ethoxy or 2-propoxy;

haloalkoxy, such as trifluoromethoxy, trichloromethoxy, fluoromethoxy, 2,2,2-trifluoroethoxy, 1,2,2-trifluoromethoxy or 1,1,2,2-tetrafluoroethoxy, in particular trifluoromethoxy or 2,2,2-trifluoroethoxy;

alkylthio, such as methylthio, ethylthio, propylthio, 2-propylthio, butylthio, 1-methylpropylthio, 2-methylpropylthio or 1,1-dimethylethylthio, in particular methylthio or ethylthio;

haloalkylthio, such as trifluoromethylthio or trichloromethylthio;

alkylsulfinyl, such as methylsulfinyl or ethylsulfinyl;

alkylsulfonyl, such as methylsulfonyl or ethylsulfonyl;

alkylcarbonyl, such as acetyl, ethylcarbonyl, propylcarbonyl, 1-methylethylcarbonyl, butylcarbonyl, 1-methylpropylcarbonyl, 2-methylpropylcarbonyl or 1,1-dimethylethylcarbonyl, in particular acetyl, 1-methylpropylcarbonyl or 1,1-dimethylethylcarbonyl;

alkoxycarbonyl, such as methoxycarbonyl, ethoxycarbonyl, propoxycarbonyl or 1-methylethoxycarbonyl;

halogen, such as fluorine, chlorine or bromine, in particular fluorine or chlorine, or carboxyl, nitro or cyano.

Particularly preferred compounds Ia and Ib are those in which $R^4$ is unsubstituted or monosubstituted or disubstituted.

Specific examples of herbicidal (hetaryloxy)- or aryloxyphenoxyacetic acid derivatives of the formula IV whose toleration by crops can be improved by aryl- or hetarylimidazolecarboxylic esters of the formulae Ia and Ib are listed in Table A below:

TABLE A $$R^a-O-\underset{}{\bigcirc}-O-\underset{R^c}{\overset{}{C}H}-CO_2R^b \quad \text{IV}$$

| No. | $R^a$ | $R^b$ | $R^c$ | Lit |
|---|---|---|---|---|
| IV.1 | 3,4-dichlorophenyl | CH₃ | CH₃ | DE-A 22 23 894 |
| IV.2 | 5-(trifluoromethyl)pyridin-2-yl | n-C₄H₉ | CH₃ | BE-A 868 875 |
| IV.3 | 2-chloro-6-(propan-2-ylideneamino-oxy)phenyl | C₂H₅ | CH₃ | BE-A 858 618 |
| IV.4 | 3-chloro-5-(trifluoromethyl)pyridin-2-yl | CH₃ | CH₃ | BE-A 868 875 |
| IV.5 | 6-chloroquinoxalin-2-yl | C₂H₅ | CH₃ | DE-A 30 04 770 |

Specific examples of cyclohexenones of the formula V whose crop plant compatibility can be improved by 1-aryl- and 1-hetarylimidazolecarboxylates of the formulae Ia and Ib are given in Table B.

TABLE B

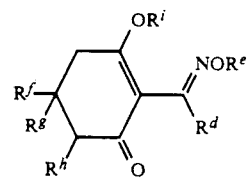

$$V$$

| No. | $R^d$ | $R^e$ | $R^f$ | $R^g$ | $R^h$ | $R^i$ | Literature |
|---|---|---|---|---|---|---|---|
| V.1 | C₃H₇ | CH₂CH=CH₂ | CH₃ | CH₃ | CO₂CH₃ | Na | DE-A 2 439 104 |
| V.2 | C₃H₇ | CH₂CH₃ | CH₂CH(CH₃)SCH₂CH₃ | H | H | H | DE-A 2 822 304 |
| V.3 | C₂H₅ | CH₂CH=CHCl | CH₂CH(CH₃)SCH₂CH₃ | H | H | H | US-A 4 440 566 |
| V.4 | C₃H₇ | CH₂CH=CHCl | CH₂CH(CH₃)SCH₂CH₃ | H | H | H | US-A 4 440 566 |
| V.5 | C₃H₇ | C₂H₅ | 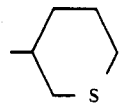 | H | H | H | EP-A 71 707 |

TABLE B-continued
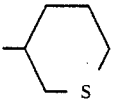
| No. | $R^d$ | $R^e$ | $R^f$ | $R^g$ | $R^h$ | $R^i$ | Literature |
|---|---|---|---|---|---|---|---|
| V.6 | $C_2H_5$ | $C_2H_5$ | 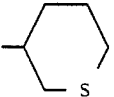 | H | H | H | EP-A 71 707 |
| V.7 | $CH_3$ | $CH_2CH=CHCH_3$ | 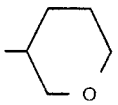 | H | H | H | EP-A 71 707 |
| V.8 | $C_3H_7$ | $C_2H_5$ | 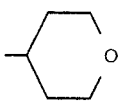 | H | H | H | EP-A 71 707 |
| V.9 | $C_2H_5$ | $CH_2CH=CHCl$ | 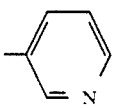 | H | H | H | EP-A 142 741 |
| V.10 | $C_3H_7$ | $C_2H_5$ | 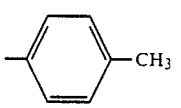 | H | H | H | EP-A 66 195 |
| V.11 | $C_2H_5$ | $C_2H_5$ | 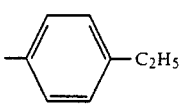 | H | H | H | DE-A 24 39 104 |
| V.12 | $C_2H_5$ | $CH_2CH=CHCH_3$ | 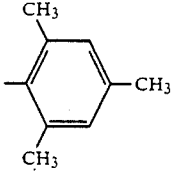 | H | H | H | DE-A 38 08 072 |
| V.13 | $C_2H_5$ | $C_2H_5$ | 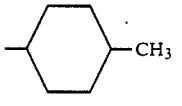 | H | H | H | EP-A 880 301 |
| V.14 | $C_3H_7$ | $CH_2CH=CHCl$ | 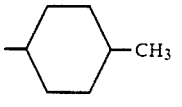 | H | H | H | EP-A 88 299 |
| V.15 | $C_3H_7$ | $CH_2CH=CHCH_3$ | 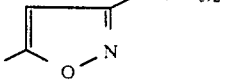 | H | H | H | EP-A 88 299 |
| V.16 | $C_2H_5$ | $CH_2CH=CHCH_3$ |  | H | H | H | EP-A 238 021 |

TABLE B-continued $$\underset{V}{\overset{OR^i}{\underset{R^h}{\overset{R^f}{\bigvee}}}}\overset{NOR^e}{\underset{O}{\bigvee}}R^d$$

| No. | $R^d$ | $R^e$ | $R^f$ | $R^g$ | $R^h$ | $R^i$ | Literature |
|---|---|---|---|---|---|---|---|
| V.17 | $C_3H_7$ | $CH_2CH=CHCH_3$ | 3-isopropyl-5-methylisoxazol-4-yl | H | H | H | EP-A 238 021 |
| V.18 | $C_2H_5$ | $CH_2CH=CHCl$ | 4-(propargyloxy)phenyl ($-OCH_2-C\equiv CH$) | H | H | H | EP-A 137 174 |
| V.19 | $C_3H_7$ | $C_2H_5$ | 4-(ethoxymethyl)phenyl ($-CH_2OC_2H_5$) | H | H | H | EP-A 2 137 200 |
| V.20 | $C_3H_7$ | $C_2H_5$ | 3,4-dibromo-3-methyltetrahydropyran-yl | H | H | H | EP-A 230 235 |
| V.21 | $C_3H_7$ | $CH_2CH=CHCl$ | 3,4-dibromo-3-methyltetrahydropyran-yl | H | H | H | EP-A 230 235 |
| V.22 | $C_3H_7$ | $CH_2CH=CHCl$ | 2,6,6-trimethylcyclohex-1-enyl | H | H | H | EP-A 46 860 |
| V.23 | $C_3H_7$ | $C_2H_5$ | cyclohexyl | H | H | H | JP-A 540 191 945 |
| V.24 | $C_3H_7$ | $C_2H_5$ | cyclohex-1-enyl | H | H | H | EP-A 46 860 |
| V.25 | $CH_3$ | $CH_2CH=CHCl$ | 4-methylcyclohexyl | H | H | H | EP-A 88 299 |
| V.26 | $C_3H_7$ | $C_2H_5$ | 4-(trifluoromethyl)phenyl | H | H | K | EP-A 137 174 |

TABLE B-continued

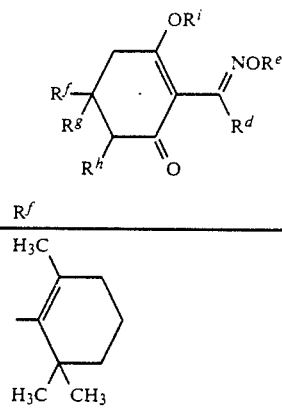

| No. | $R^d$ | $R^e$ | $R^f$ | $R^g$ | $R^h$ | $R^i$ | Literature |
|---|---|---|---|---|---|---|---|
| V.27 | $C_2H_5$ | $CH_2CH=CHCl$ | (2,6,6-trimethylcyclohex-1-enyl) | H | H | H | EP-A 46 860 |

The herbicidal active ingredients and antidotes may be applied together or separately to the leaves and shoots of the crop plants and unwanted plants. Preferably, the antidote is applied together with the herbicidal active ingredient. If the components are applied separately, the antidote is applied first to the field and then the herbicidal active ingredient. The herbicidal active ingredient and antidote may be formulated together or separately as spray agents in the form of suspensions, emulsions or solutions.

Treatment of the crop plant seed with the antidote prior to sowing is also feasible. The herbicidal active ingredient is then applied to the field on its own in conventional manner.

For herbicidal (heteroaryloxy)-phenoxyacetic or -propionic acid derivatives of the formula IV, the amount of antidotally active compound varies, depending on the crop. The ratios may vary over a wide range, and are also dependent on the structure of the (heteroaryloxy)phenoxyacetic or -propionic acid derivatives IV and on the crop involved. Suitable ratios of herbicidal active ingredient to antidote are from 1:4 to 1:0.01, and preferably from 1:4 to 1:0.1, parts by weight.

For the same cyclohexenone derivative V, the amount of antidote varies, depending on the crop. The ratios in which a cyclohexenone derivative V and an aryl- or heteroarylimidazolecarboxylate of the formula Ia and/or Ib are used may vary over a wide range, and are dependent on the structure of the cyclohexenone derivative, the aryl- or heteroarylimidazolecarboxylate of the formula Ia and/or Ib and the crop involved. Suitable ratios of herbicidal active ingredient to safener are from 1:4 to 1:0.01, and preferably from 1:4 to 1:0.25, parts by weight.

The novel herbicidal agents may contain, in addition to the aryl- or heteroarylimidazolecarboxylate of the formula Ia and/or Ib as safener and the herbicide from the group of the (heteroaryloxy)phenoxyacetic acids IV or cyclohexenones V, other herbicidal or growth-regulating active ingredients and inert additives without the safening effect being impaired.

The agents according to the invention, or—when applied separately—the herbicidal active ingredients and the safener, are applied for instance in the form of directly sprayable solutions, powders, suspensions (including high-percentage aqueous, oily or others), dispersions, emulsions, oil dispersions, pastes, dusts, broadcasting agents or granules by spraying, atomizing, dusting, broadcasting or pouring. The forms of application depend entirely on the purpose for which the active ingredients are to be used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, cyclohexanol, cyclohexanone, chlorobenzene, isophorone, etc., and strongly polar solvents such as N,N-dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of aromatic sulfonic acids, e.g., ligninsulfonic acid, phenolsulfonic acid, naphthalenesulfonic acid and dibutylnaphthalenesulfonic acid, and of fatty acids, alkyl and alkylaryl sulfonates, and alkyl, lauryl ether and fatty alcohol sulfates, alkali metal and alkaline earth metal salts of dibutylnaphthalenesulfonic acid, lauryl ether sulfate, fatty alcohol sulfates, and salts of sulfated hexadecanols, heptadecanols, and octadecanols, salts of fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin-sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, attapulgus clay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain meals, bark meal, wood meal, and nutshell meal, cellulosic powders, etc.

MANUFACTURING EXAMPLES

The directions given in the examples below may be used, after appropriate modifications of the starting materials, to obtain further compounds of the formula Ia and Ib. The compounds obtained are listed with their physical data in the tables below; compounds without these data may be prepared from the appropriate materials in analogous manner. In view of their close structural relationship to the compounds which have been manufactured and investigated, they are expected to have a similar action.

EXAMPLE 1

Ethyl 1-(2,4-dinitrophenyl)-2-methylimidazole-4-carboxylate 16 ml of triethylamine was added to 14.5 g (0.078 mol) of 2,4-dinitrofluorobenzene, 12 g (0.078 mol) of ethyl 2-methylimidazole-4-carboxylate and 500 ml of toluene, and the mixture was refluxed for 18 hours. The solvent was then distilled off under reduced pressure and the residue was chromatographed using pentane/ethyl acetate as mobile phase.

Yield: 19.5 g (81% of theory); m.p.: 150°-152° C. (Active ingredient example 1.015).

EXAMPLE 2

Isopropyl 1-(2,4-dinitrophenyl)-2-bromo-5-methyl-4-imidazolecarboxylate 4.2 ml of triethylamine was added dropwise to 5 g (0.02 mol) of isopropyl 2-bromo-5-methyl-4-imidazolecarboxylate, 3.9 g of 1-fluoro-2,4-dinitrobenzene and 200 ml of toluene, and the mixture was refluxed for 16 hours. The toluene solution was then washed with water, dried and concentrated. The residue was stirred with diethyl ether and the solid obtained in this manner was isolated.

Yield: 5.7 g (69%); m.p.: 161°-162° C. (Active ingredient example 1.025).

EXAMPLE 3

Methyl 1-(2,4-dibromophenyl)-2-methylimidazole-4-carboxylate 14.1 g of 30% strength sodium methylate solution was added to 10.9 g (0.078 mol) of methyl 2-methylimidazole-4-carboxylate in 100 ml of dimethylformamide; the methanol which formed was removed completely. 38.1 g (0.15 mol) of 1-fluoro-2,4-dibromobenzene was added to the dimethylformamide solution remaining, and the mixture was refluxed for 2 hours. Water was then added, extraction carried out with ethyl acetatem and the ethyl acetate phase was washed with water. After removal of the solvent from the organic phase, there was obtained a residue which crystallized on trituration with diisopropyl ether.

Yield: 10.8 g (36.7%); m.p.: 162°-163° C. (Active ingredient example 1.059).

EXAMPLE 4

Ethyl 1-(2,4-dinitrophenyl)-2-methyl-5-chloroimidazole-4-carboxylate and ethyl 1-(2,4-dinitrophenyl)-2-trichloromethyl-5-chloroimidazole-4-carboxylate 16.5 g (0.1225 mol) of sulfuryl chloride and 0.2 g of dibenzoyl peroxide were added to 9.8 g (0.03 mol) of ethyl 1-(2,4-dinitrophenyl)-2-methylimidazole-4-carboxylate in 200 ml of chlorobenzene, and the mixture was heated at 100° C. for 90 minutes. When gas evolution had ceased, the mixture was concentrated to dryness, the residue was adjusted to a pH of 7 with dilute aqueous ammonia and extracted with methylene chloride, and the organic phase was dried with sodium sulfate, concentrated and chromatographed.

Yield: 4.7 g (43% of theory); m.p.: 181°-182° C. (Active ingredient example 2.001).

TABLE 1

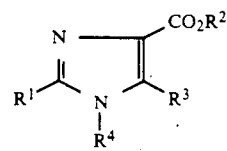

| No. | $R^1$ | $R^2$ | $R^3$ | $R^4$ | mp (°C.); NMR(ppm) |
|---|---|---|---|---|---|
| 1.001 | $CH_3$ | $CH_3$ | H | phenyl | |
| 1.002 | $CH_3$ | $CH_2CH_3$ | H | phenyl | |
| 1.003 | Cl | $CH_3$ | $CH_3$ | phenyl | |
| 1.004 | Cl | $CH_2CH_3$ | $CH_3$ | phenyl | |
| 1.005 | Cl | $CH(CH_3)_2$ | $CH_3$ | phenyl | |
| 1.006 | Br | $CH_3$ | $CH_3$ | phenyl | |
| 1.007 | Br | $CH_2CH_3$ | $CH_3$ | phenyl | |
| 1.008 | $CH_3$ | $CH_3$ | H | 4-nitrophenyl | |
| 1.009 | $CH_3$ | $CH_2CH_3$ | H | 4-nitrophenyl | |
| 1.010 | $CH_3$ | $CH(CH_3)_2$ | H | 4-nitrophenyl | |
| 1.011 | $CH_3$ | $CH_2CH=CH_2$ | H | 4-nitrophenyl | |
| 1.012 | Cl | $CH_2CH_3$ | $CH_3$ | 4-nitrophenyl | |
| 1.013 | Br | $CH_2CH_3$ | $CH_3$ | 4-nitrophenyl | |
| 1.014 | $CH_3$ | $CH_3$ | H | 2,4-dinitrophenyl | |

TABLE 1-continued

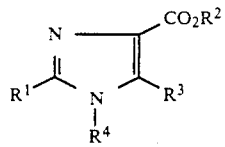

| No. | $R^1$ | $R^2$ | $R^3$ | $R^4$ | mp (°C.); NMR(ppm) |
|---|---|---|---|---|---|
| 1.015 | $CH_3$ | $CH_2CH_3$ | H | 2,4-dinitrophenyl | 150–152 |
| 1.016 | $CH_3$ | $CH(CH_3)_2$ | H | 2,4-dinitrophenyl | |
| 1.017 | $CH_3$ | $CH_2CH_2CH_3$ | H | 2,4-dinitrophenyl | |
| 1.018 | $CH_3$ | $CH_2CH=CH_2$ | H | 2,4-dinitrophenyl | |
| 1.019 | $CH_3$ | $CH_2C\equiv CH$ | H | 2,4-dinitrophenyl | |
| 1.020 | Cl | $CH_3$ | $CH_3$ | 2,4-dinitrophenyl | |
| 1.021 | Cl | $CH_2CH_3$ | $CH_3$ | 2,4-dinitrophenyl | |
| 1.022 | Cl | $CH(CH_3)_2$ | $CH_3$ | 2,4-dinitrophenyl | |
| 1.023 | Br | $CH_3$ | $CH_3$ | 2,4-dinitrophenyl | |
| 1.024 | Br | $CH_2CH_3$ | $CH_3$ | 2,4-dinitrophenyl | 148–150 |
| 1.025 | Br | $CH(CH_3)_2$ | $CH_3$ | 2,4-dinitrophenyl | 161–162 |
| 1.026 | $CH_3$ | $CH_3$ | H | 2-nitrophenyl | |
| 1.027 | $CH_3$ | $CH_2CH_3$ | H | 2-nitrophenyl | |
| 1.028 | Cl | $CH_2CH_3$ | $CH_3$ | 2-nitrophenyl | |
| 1.029 | Br | $CH_2CH_3$ | $CH_3$ | 2-nitrophenyl | |
| 1.030 | $CH_3$ | $CH_3$ | H | 4-chlorophenyl | |
| 1.031 | $CH_3$ | $CH_2CH_3$ | H | 4-chlorophenyl | |
| 1.032 | Cl | $CH_3$ | $CH_3$ | 4-chlorophenyl | |
| 1.033 | Cl | $CH_2CH_3$ | $CH_3$ | 4-chlorophenyl | |
| 1.034 | Br | $CH_3$ | $CH_3$ | 4-chlorophenyl | |
| 1.035 | Br | $CH_2CH_3$ | $CH_3$ | 4-chlorophenyl | |
| 1.036 | $CH_3$ | $CH_3$ | H | 2-chlorophenyl | |
| 1.037 | $CH_3$ | $CH_2CH_3$ | H | 2-chlorophenyl | |
| 1.038 | $CH_3$ | $CH_3$ | H | 2,4-dichlorophenyl | 162–163 |
| 1.039 | $CH_3$ | $CH_2CH_3$ | H | 2,4-dichlorophenyl | 121–122 |
| 1.040 | $CH_3$ | $CH_2CH_2CH_3$ | H | 2,4-dichlorophenyl | |
| 1.041 | $CH_3$ | $CH(CH_3)_2$ | H | 2,4-dichlorophenyl | |
| 1.042 | Cl | $CH_3$ | $CH_3$ | 2,4-dichlorophenyl | |
| 1.043 | Cl | $CH_2CH_3$ | $CH_3$ | 2,4-dichlorophenyl | |
| 1.044 | Cl | $CH(CH_3)_2$ | $CH_3$ | 2,4-dichlorophenyl | |
| 1.045 | Cl | cyclopentyl | $CH_3$ | 2,4-dichlorophenyl | |
| 1.046 | Cl | cyclohexyl | $CH_3$ | 2,4-dichlorophenyl | |
| 1.047 | Br | $CH_3$ | $CH_3$ | 2,4-dichlorophenyl | |
| 1.048 | Br | $CH_2CH_3$ | $CH_3$ | 2,4-dichlorophenyl | |
| 1.049 | Br | $CH_2CH_2CH_3$ | $CH_3$ | 2,4-dichlorophenyl | |
| 1.050 | Br | $CH(CH_3)_2$ | $CH_3$ | 2,4-dichlorophenyl | |
| 1.051 | $CH_3$ | $CH_3$ | H | 4-bromophenyl | |
| 1.052 | $CH_3$ | $CH_2CH_3$ | H | 4-bromophenyl | |
| 1.053 | Cl | $CH_2CH_3$ | $CH_3$ | 4-bromophenyl | |
| 1.054 | Br | $CH_2CH_3$ | $CH_3$ | 4-bromophenyl | |
| 1.055 | $CH_3$ | $CH_3$ | H | 2-bromophenyl | |
| 1.056 | $CH_3$ | $CH_2CH_3$ | H | 2-bromophenyl | |
| 1.057 | Cl | $CH_2CH_3$ | $CH_3$ | 2-bromophenyl | |
| 1.058 | Br | $CH_2CH_3$ | $CH_3$ | 2-bromophenyl | |
| 1.059 | $CH_3$ | $CH_3$ | H | 2,4-dibromophenyl | 162–163 |
| 1.060 | $CH_3$ | $CH_2CH_3$ | H | 2,4-dibromophenyl | |
| 1.061 | $CH_3$ | $CH_2CH_2CH_3$ | H | 2,4-dibromophenyl | |
| 1.062 | $CH_3$ | $CH(CH_3)_2$ | H | 2,4-dibromophenyl | |
| 1.063 | Cl | $CH_2CH_3$ | $CH_3$ | 2,4-dibromophenyl | |
| 1.064 | Cl | $CH(CH_3)_2$ | $CH_3$ | 2,4-dibromophenyl | |
| 1.065 | Br | $CH_2CH_3$ | $CH_3$ | 2,4-dibromophenyl | |
| 1.066 | Br | $CH(CH_3)_2$ | $CH_3$ | 2,4-dibromophenyl | |
| 1.067 | $CH_3$ | $CH_3$ | H | 2,4,6-trichlorophenyl | |
| 1.068 | $CH_3$ | $CH_2CH_3$ | H | 2,4,6-trichlorophenyl | |
| 1.069 | $CH_3$ | $CH_2CH_2CH_3$ | H | 2,4,6-trichlorophenyl | |
| 1.070 | Cl | $CH_2CH_3$ | $CH_3$ | 2,4,6-trichlorophenyl | |
| 1.071 | Br | $CH_2CH_3$ | $CH_3$ | 2,4,6-trichlorophenyl | |
| 1.072 | Br | $CH_2CH_2CH_3$ | $CH_3$ | 2,4,6-trichlorophenyl | |
| 1.073 | $CH_3$ | $CH_3$ | H | 4-cyanophenyl | |
| 1.074 | $CH_3$ | $CH_2CH_3$ | H | 4-cyanophenyl | |
| 1.075 | $CH_3$ | $CH_2CH_2CH_3$ | H | 4-cyanophenyl | |
| 1.076 | $CH_3$ | $CH(CH_3)_2$ | H | 4-cyanophenyl | |
| 1.077 | Cl | $CH_2CH_3$ | $CH_3$ | 4-cyanophenyl | |
| 1.078 | Cl | $CH(CH_3)_2$ | $CH_3$ | 4-cyanophenyl | |
| 1.079 | Br | $CH_2CH_3$ | $CH_3$ | 4-cyanophenyl | |
| 1.080 | Br | $CH(CH_3)_2$ | $CH_3$ | 4-cyanophenyl | |
| 1.081 | $CH_3$ | $CH_3$ | H | 2,4-dicyanophenyl | |
| 1.082 | $CH_3$ | $CH_2CH_3$ | H | 2,4-dicyanophenyl | |
| 1.083 | Cl | $CH_2CH_3$ | $CH_3$ | 2,4-dicyanophenyl | |
| 1.084 | Br | $CH_2CH_3$ | $CH_3$ | 2,4-dicyanophenyl | |
| 1.085 | $CH_3$ | $CH_3$ | H | 4-trifluoromethylphenyl | |
| 1.086 | $CH_3$ | $CH_2CH_3$ | H | 4-trifluoromethylphenyl | |
| 1.087 | $CH_3$ | $CH_2CH_2CH_3$ | H | 4-trifluoromethylphenyl | |

TABLE 1-continued $$\underset{R^4}{\underset{|}{N}}\underset{R^3}{\overset{N}{\underset{}{\bigwedge}}}\overset{CO_2R^2}{}$$

| No. | $R^1$ | $R^2$ | $R^3$ | $R^4$ | mp (°C.); NMR(ppm) |
|---|---|---|---|---|---|
| 1.088 | Cl | $CH_2CH_3$ | $CH_3$ | 4-trifluoromethylphenyl | |
| 1.089 | Br | $CH_2CH_3$ | $CH_3$ | 4-trifluoromethylphenyl | |
| 1.090 | $CH_3$ | $CH_3$ | H | 4-chloro-2-nitrophenyl | |
| 1.091 | $CH_3$ | $CH_2CH_3$ | H | 4-chloro-2-nitrophenyl | |
| 1.092 | Cl | $CH_2CH_3$ | $CH_3$ | 4-chloro-2-nitrophenyl | |
| 1.093 | Br | $CH_2CH_3$ | $CH_3$ | 4-chloro-2-nitrophenyl | |
| 1.094 | $CH_3$ | $CH_3$ | H | 4-chloro-2-fluorophenyl | |
| 1.095 | $CH_3$ | $CH_2CH_3$ | H | 4-chloro-2-fluorophenyl | |
| 1.096 | Cl | $CH_2CH_3$ | $CH_3$ | 4-chloro-2-fluorophenyl | |
| 1.097 | Br | $CH_2CH_3$ | $CH_3$ | 4-chloro-2-fluorophenyl | |
| 1.098 | $CH_3$ | $CH_3$ | H | 4-chloro-2-cyanophenyl | |
| 1.099 | $CH_3$ | $CH_2CH_3$ | H | 4-chloro-2-cyanophenyl | |
| 1.100 | Cl | $CH_2CH_3$ | $CH_3$ | 4-chloro-2-cyanophenyl | |
| 1.101 | Br | $CH_2CH_3$ | $CH_3$ | 4-chloro-2-cyanophenyl | |
| 1.102 | $CH_3$ | $CH_3$ | H | 4-chloro-2-trifluoromethylphenyl | |
| 1.103 | $CH_3$ | $CH_2CH_3$ | H | 4-chloro-2-trifluoromethylphenyl | |
| 1.104 | Cl | $CH_2CH_3$ | $CH_3$ | 4-chloro-2-trifluoromethylphenyl | |
| 1.105 | Br | $CH_2CH_3$ | $CH_3$ | 4-chloro-2-trifluoromethylphenyl | |
| 1.106 | $CH_3$ | $CH_3$ | H | 4-chloro-2-methylphenyl | |
| 1.107 | $CH_3$ | $CH_2CH_3$ | H | 4-chloro-2-methylphenyl | |
| 1.108 | Cl | $CH_2CH_3$ | $CH_3$ | 4-chloro-2-methylphenyl | |
| 1.109 | Br | $CH_2CH_3$ | $CH_3$ | 4-chloro-2-methylphenyl | |
| 1.110 | $CH_3$ | $CH_3$ | H | 4-bromo-2-nitrophenyl | |
| 1.111 | $CH_3$ | $CH_2CH_3$ | H | 4-bromo-2-nitrophenyl | |
| 1.112 | Cl | $CH_2CH_3$ | $CH_3$ | 4-bromo-2-nitrophenyl | |
| 1.113 | Br | $CH_2CH_3$ | $CH_3$ | 4-bromo-2-nitrophenyl | |
| 1.114 | $CH_3$ | $CH_3$ | H | 4-bromo-2-chlorophenyl | |
| 1.115 | $CH_3$ | $CH_2CH_3$ | H | 4-bromo-2-chlorophenyl | |
| 1.116 | Cl | $CH_2CH_3$ | $CH_3$ | 4-bromo-2-chlorophenyl | |
| 1.117 | Br | $CH_2CH_3$ | $CH_3$ | 4-bromo-2-chlorophenyl | |
| 1.118 | $CH_3$ | $CH_3$ | H | 4-bromo-2-fluorophenyl | |
| 1.119 | $CH_3$ | $CH_2CH_3$ | H | 4-bromo-2-fluorophenyl | |
| 1.120 | Cl | $CH_2CH_3$ | $CH_3$ | 4-bromo-2-fluorophenyl | |
| 1.121 | Br | $CH_2CH_3$ | $CH_3$ | 4-bromo-2-fluorophenyl | |
| 1.122 | $CH_3$ | $CH_3$ | H | 4-bromo-2-cyanophenyl | |
| 1.123 | $CH_3$ | $CH_2CH_3$ | H | 4-bromo-2-cyanophenyl | |
| 1.124 | Cl | $CH_2CH_3$ | $CH_3$ | 4-bromo-2-cyanophenyl | |
| 1.125 | Br | $CH_2CH_3$ | $CH_3$ | 4-bromo-2-cyanophenyl | |
| 1.126 | $CH_3$ | $CH_3$ | H | 4-bromo-2-trifluoromethylphenyl | |
| 1.127 | $CH_3$ | $CH_2CH_3$ | H | 4-bromo-2-trifluoromethylphenyl | |
| 1.128 | Cl | $CH_2CH_3$ | $CH_3$ | 4-bromo-2-trifluoromethylphenyl | |
| 1.129 | Br | $CH_2CH_3$ | $CH_3$ | 4-bromo-2-trifluoromethyphenyl | |
| 1.130 | $CH_3$ | $CH_3$ | H | 4-bromo-2-methylphenyl | |
| 1.131 | $CH_3$ | $CH_2CH_3$ | H | 4-bromo-2-methylphenyl | |
| 1.132 | Cl | $CH_2CH_3$ | $CH_3$ | 4-bromo-2-methylphenyl | |
| 1.133 | Br | $CH_2CH_3$ | $CH_3$ | 4-bromo-2-methylphenyl | |
| 1.134 | $CH_3$ | $CH_3$ | H | 4-cyano-2-nitrophenyl | |
| 1.135 | $CH_3$ | $CH_2CH_3$ | H | 4-cyano-2-nitrophenyl | |
| 1.136 | Cl | $CH_2CH_3$ | $CH_3$ | 4-cyano-2-nitrophenyl | |
| 1.137 | Br | $CH_2CH_3$ | $CH_3$ | 4-cyano-2-nitrophenyl | |
| 1.138 | $CH_3$ | $CH_3$ | H | 4-cyano-2-chlorophenyl | |
| 1.139 | $CH_3$ | $CH_2CH_3$ | H | 4-cyano-2-chlorophenyl | |
| 1.140 | Cl | $CH_2CH_3$ | $CH_3$ | 4-cyano-2-chlorophenyl | |
| 1.141 | Br | $CH_2CH_3$ | $CH_3$ | 4-cyano-2-chlorophenyl | |
| 1.142 | $CH_3$ | $CH_3$ | H | 4-cyano-2-fluorophenyl | |
| 1.143 | $CH_3$ | $CH_2CH_3$ | H | 4-cyano-2-fluorophenyl | |
| 1.144 | Cl | $CH_2CH_3$ | $CH_3$ | 4-cyano-2-fluorophenyl | |
| 1.145 | Br | $CH_2CH_3$ | $CH_3$ | 4-cyano-2-fluorophenyl | |
| 1.146 | $CH_3$ | $CH_3$ | H | 4-cyano-2-bromophenyl | |
| 1.147 | $CH_3$ | $CH_2CH_3$ | H | 4-cyano-2-bromophenyl | 171-173 |
| 1.148 | $CH_3$ | $CH_2CH_2CH_3$ | H | 4-cyano-2-bromophenyl | |
| 1.149 | $CH_3$ | $CH(CH_3)_2$ | H | 4-cyano-2-bromophenyl | |
| 1.150 | Cl | $CH_2CH_3$ | $CH_3$ | 4-cyano-2-bromophenyl | |
| 1.151 | Cl | $CH(CH_3)_2$ | $CH_3$ | 4-cyano-2-bromophenyl | |
| 1.152 | Cl | Cyclopentyl | $CH_3$ | 4-cyano-2-bromophenyl | |

TABLE 1-continued $$\underset{R^4}{\underset{|}{N}}\underset{N}{\overset{N}{\diagup}}\overset{CO_2R^2}{\underset{R^3}{\diagdown}}$$

| No. | $R^1$ | $R^2$ | $R^3$ | $R^4$ | mp (°C.); NMR(ppm) |
|---|---|---|---|---|---|
| 1.153 | Cl | Cyclohexyl | $CH_3$ | 4-cyano-2-bromophenyl | |
| 1.154 | Br | $CH_2CH_3$ | $CH_3$ | 4-cyano-2-bromophenyl | |
| 1.155 | $CH_3$ | $CH_3$ | H | 4-cyano-2-methylphenyl | |
| 1.156 | $CH_3$ | $CH_2CH_3$ | H | 4-cyano-2-methylphenyl | |
| 1.157 | Cl | $CH_2CH_3$ | $CH_3$ | 4-cyano-2-methylphenyl | |
| 1.158 | Br | $CH_2CH_3$ | $CH_3$ | 4-cyano-2-methylphenyl | |
| 1.159 | $CH_3$ | $CH_3$ | H | 4-cyano-2-trifluoromethylphenyl | |
| 1.160 | $CH_3$ | $CH_2CH_3$ | H | 4-cyano-2-trifluoromethylphenyl | |
| 1.161 | Cl | $CH_2CH_3$ | $CH_3$ | 4-cyano-2-trifluoromethylphenyl | |
| 1.162 | Br | $CH_2CH_3$ | $CH_3$ | 4-cyano-2-trifluoromethylphenyl | |
| 1.163 | $CH_3$ | $CH_3$ | H | 4-nitro-2-chlorophenyl | |
| 1.164 | $CH_3$ | $CH_2CH_3$ | H | 4-nitro-2-chlorophenyl | 128–129 |
| 1.165 | Cl | $CH_2CH_3$ | $CH_3$ | 4-nitro-2-chlorophenyl | |
| 1.166 | Br | $CH_2CH_3$ | $CH_3$ | 4-nitro-2-chlorophenyl | |
| 1.167 | $CH_3$ | $CH_3$ | H | 4-nitro-2-bromophenyl | |
| 1.168 | $CH_3$ | $CH_2CH_3$ | H | 4-nitro-2-bromophenyl | |
| 1.169 | Cl | $CH_2CH_3$ | $CH_3$ | 4-nitro-2-bromophenyl | |
| 1.170 | Br | $CH_2CH_3$ | $CH_3$ | 4-nitro-2-bromophenyl | |
| 1.171 | $CH_3$ | $CH_3$ | H | 4-nitro-2-cyanophenyl | |
| 1.172 | $CH_3$ | $CH_2CH_3$ | H | 4-nitro-2-cyanophenyl | |
| 1.173 | Cl | $CH_2CH_3$ | $CH_3$ | 4-nitro-2-cyanophenyl | |
| 1.174 | Br | $CH_2CH_3$ | $CH_3$ | 4-nitro-2-cyanophenyl | |
| 1.175 | $CH_3$ | $CH_3$ | H | 4-trifluoromethyl-2-chlorophenyl | |
| 1.176 | $CH_3$ | $CH_2CH_3$ | H | 4-trifluoromethyl-2-chlorophenyl | |
| 1.177 | Cl | $CH_2CH_3$ | $CH_3$ | 4-trifluoromethyl-2-chlorophenyl | |
| 1.178 | Br | $CH_2CH_3$ | $CH_3$ | 4-trifluoromethyl-2-chlorophenyl | |
| 1.179 | $CH_3$ | $CH_3$ | H | 4-trifluoromethyl-2-bromophenyl | |
| 1.180 | $CH_3$ | $CH_2CH_3$ | H | 4-trifluoromethyl-2-bromophenyl | |
| 1.181 | Cl | $CH_2CH_3$ | $CH_3$ | 4-trifluoromethyl-2-bromophenyl | |
| 1.182 | Br | $CH_2CH_3$ | $CH_3$ | 4-trifluoromethyl-2-bromophenyl | |
| 1.183 | $CH_3$ | $CH_3$ | H | 4-trifluoromethyl-2-cyanophenyl | |
| 1.184 | $CH_3$ | $CH_2CH_3$ | H | 4-trifluoromethyl-2-cyanophenyl | |
| 1.185 | Cl | $CH_2CH_3$ | $CH_3$ | 4-trifluoromethyl-2-cyanophenyl | |
| 1.186 | Br | $CH_2CH_3$ | $CH_3$ | 4-trifluoromethyl-2-cyanophenyl | |
| 1.187 | $CH_3$ | $CH_3$ | H | 4-tert-butyl-2-chlorophenyl | |
| 1.188 | $CH_3$ | $CH_2CH_3$ | H | 4-tert-butyl-2-chlorophenyl | |
| 1.189 | Cl | $CH_2CH_3$ | $CH_3$ | 4-tert-butyl-2-chlorophenyl | |
| 1.190 | Br | $CH_2CH_3$ | $CH_3$ | 4-tert-butyl-2-chlorophenyl | |
| 1.191 | $CH_3$ | $CH_3$ | H | 4-tert-butyl-2-bromophenyl | |
| 1.192 | $CH_3$ | $CH_2CH_3$ | H | 4-tert-butyl-2-bromophenyl | |
| 1.193 | Cl | $CH_2CH_3$ | $CH_3$ | 4-tert-butyl-2-bromophenyl | |
| 1.194 | Br | $CH_2CH_3$ | $CH_3$ | 4-tert-butyl-2-bromphenyl | |
| 1.195 | $CH_3$ | $CH_3$ | H | 4-tert-butyl-2-cyanophenyl | |
| 1.196 | $CH_3$ | $CH_2CH_3$ | H | 4-tert-butyl-2-cyanophenyl | |
| 1.197 | Cl | $CH_2CH_3$ | $CH_3$ | 4-tert-butyl-2-cyanophenyl | |
| 1.198 | Br | $CH_2CH_3$ | $CH_3$ | 4-tert-butyl-2- | |

TABLE 1-continued $$\underset{R^4}{\underset{|}{R^1}}\overset{N}{\underset{N}{\bigvee}}\overset{CO_2R^2}{\underset{R^3}{}}$$

| No. | $R^1$ | $R^2$ | $R^3$ | $R^4$ | mp (°C.); NMR(ppm) |
|---|---|---|---|---|---|
| 1.199 | $CH_3$ | $CH_3$ | H | 2,6-dichloro-4-tri-fluoromethylphenyl cyanophenyl | |
| 1.200 | $CH_3$ | $CH_2CH_3$ | H | 2,6-dichloro-4-tri-fluoromethylphenyl | |
| 1.201 | Cl | $CH_2CH_3$ | $CH_3$ | 2,6-dichloro-4-tri-fluoromethylphenyl | |
| 1.202 | Br | $CH_2CH_3$ | $CH_3$ | 2,6-dichloro-4-tri-fluoromethylphenyl | |
| 1.203 | $CH_3$ | $CH_3$ | H | 2,6-dichloro-4-nitrophenyl | 205–207 |
| 1.204 | $CH_3$ | $CH_2CH_3$ | H | 2,6-dichloro-4-nitrophenyl | 149–151 |
| 1.205 | Cl | $CH_2CH_3$ | $CH_3$ | 2,6-dichloro-4-nitrophenyl | |
| 1.206 | Br | $CH_2CH_3$ | $CH_3$ | 2,6-dichloro-4-nitrophenyl | |
| 1.207 | $CH_3$ | $CH_3$ | H | 2,6-dinitro-4-tri-fluoromethylphenyl | |
| 1.208 | $CH_3$ | $CH_2CH_3$ | H | 2,6-dinitro-4-tri-fluoromethylphenyl | |
| 1.209 | Cl | $CH_2CH_3$ | $CH_3$ | 2,6-dinitro-4-tri-fluoromethylphenyl | |
| 1.210 | Br | $CH_2CH_3$ | $CH_3$ | 2,6-dinitro-4-tri-fluoromethylphenyl | |
| 1.211 | $CH_3$ | $CH_3$ | H | 2,4-dinitro-6-cyano-phenyl | |
| 1.212 | $CH_3$ | $CH_2CH_3$ | H | 2,4-dinitro-6-cyano-phenyl | |
| 1.213 | Cl | $CH_2CH_3$ | $CH_3$ | 2,4-dinitro-6-cyano-phenyl | |
| 1.214 | Br | $CH_2CH_3$ | $CH_3$ | 2,4-dinitro-6-cyano-phenyl | |
| 1.215 | $CH_3$ | $CH_3$ | H | 2,4-dinitro-6-tri-fluoromethylphenyl | |
| 1.216 | $CH_3$ | $CH_2CH_3$ | H | 2,4-dinitro-6-tri-fluoromethylphenyl | |
| 1.217 | Cl | $CH_2CH_3$ | $CH_3$ | 2,4-dinitro-6-tri-fluoromethylphenyl | |
| 1.218 | Br | $CH_2CH_3$ | $CH_3$ | 2,4-dinitro-6-tri-fluoromethylphenyl | |
| 1.219 | $CH_3$ | $CH_3$ | H | 2,4-dinitro-6-carb-ethoxyphenyl | |
| 1.220 | $CH_3$ | $CH_2CH_3$ | H | 2,4-dinitro-6-carb-ethoxyphenyl | |
| 1.221 | Cl | $CH_2CH_3$ | $CH_3$ | 2,4-dinitro-6-carb-ethoxyphenyl | |
| 1.222 | Br | $CH_2CH_3$ | $CH_3$ | 2,4-dinitro-6-carb-ethoxyphenyl | |
| 1.223 | $CH_3$ | $CH_3$ | H | 2-nitro-4-carb-ethoxyphenyl | |
| 1.224 | $CH_3$ | $CH_2CH_3$ | H | 2-nitro-4-carb-ethoxyphenyl | |
| 1.225 | Cl | $CH_2CH_3$ | $CH_3$ | 2-nutro-4-carb-ethoxyphenyl | |
| 1.226 | Br | $CH_2CH_3$ | $CH_3$ | 2-nitro-4-carb-ethoxyphenyl | |
| 1.227 | $CH_3$ | $CH_3$ | H | 2-nitro-4-acetyl-phenyl | |
| 1.228 | $CH_3$ | $CH_2CH_3$ | H | 2-nitro-4-acetyl-phenyl | |
| 1.229 | Cl | $CH_2CH_3$ | $CH_3$ | 2-nitro-4-acetylphenyl | |
| 1.230 | Br | $CH_2CH_3$ | $CH_3$ | 2-nitro-4-acetylphenyl | |
| 1.231 | $CH_3$ | $CH_3$ | H | 2-chloro-4-acetylphenyl | |
| 1.232 | $CH_3$ | $CH_2CH_3$ | H | 2-chloro-4-acetylphenyl | |
| 1.233 | Cl | $CH_2CH_3$ | $CH_3$ | 2-chloro-4-acetylphenyl | |
| 1.234 | Br | $CH_2CH_3$ | $CH_3$ | 2-chloro-4-acetylphenyl | |
| 1.235 | $CH_3$ | $CH_3$ | H | 2,4-dinitro-6-chlorophenyl | |
| 1.236 | $CH_3$ | $CH_2CH_3$ | H | 2,4-dinitro-6-chlorophenyl | |
| 1.237 | Cl | $CH_2CH_3$ | $CH_3$ | 2,4-dinitro-6-chlorophenyl | |
| 1.238 | Br | $CH_2CH_3$ | $CH_3$ | 2,4-dinitro-6-chlorophenyl | |
| 1.239 | $CH_3$ | $CH_3$ | H | 2,6-dinitro-4-methyl-sulfonylphenyl | |

TABLE 1-continued

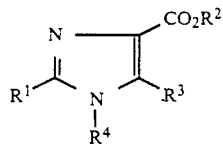

| No. | R¹ | R² | R³ | R⁴ | mp (°C.); NMR(ppm) |
|---|---|---|---|---|---|
| 1.240 | CH₃ | CH₂CH₃ | H | 2,6-dinitro-4-methyl-sulfonylphenyl | |
| 1.241 | Cl | CH₂CH₃ | CH₃ | 2,6-dinitro-4-methyl-sulfonylphenyl | |
| 1.242 | Br | CH₂CH₃ | CH₃ | 2,6-dinitro-4-methyl-sulfonylphenyl | |
| 1.243 | CH₃ | CH₃ | H | 2,6-dinitro-4-carbomethoxyphenyl | |
| 1.244 | CH₃ | CH₂CH₃ | H | 2,6-dinitro-4-carbomethoxyphenyl | |
| 1.245 | Cl | CH₂CH₃ | CH₃ | 2,6-dinitro-4-carbomethoxyphenyl | |
| 1.246 | Br | CH₂CH₃ | CH₃ | 2,6-dinitro-4-carbomethoxyphenyl | |
| 1.247 | CH₃ | CH₃ | H | 2,6-dinitro-4-methylphenyl | |
| 1.248 | CH₃ | CH₂CH₃ | H | 2,6-dinitro-4-methylphenyl | |
| 1.249 | Cl | CH₂CH₃ | CH₃ | 2,6-dinitro-4-methylphenyl | |
| 1.250 | Br | CH₂CH₃ | CH₃ | 2,6-dinitro-4-methylphenyl | |
| 1.251 | CH₃ | CH₃ | H | 3,5-dichloro-4-pyridyl | |
| 1.252 | CH₃ | CH₃ | H | 3,5-dichloro-4-pyridyl | |
| 1.253 | Cl | CH₂CH₃ | CH₃ | 3,5-dichloro-4-pyridyl | |
| 1.254 | Br | CH₂CH₃ | CH₃ | 3,5-dichloro-4-pyridyl | |
| 1.255 | CH₃ | CH₃ | H | 3-chloro-5-trifluoromethyl-2-pyridyl | |
| 1.256 | CH₃ | CH₂CH₃ | H | 3-chloro-5-trifluoromethyl-2-pyridyl | |
| 1.257 | Cl | CH₂CH₃ | CH₃ | 3-chloro-5-trifluoromethyl-2-pyridyl | |
| 1.258 | Br | CH₂CH₃ | CH₃ | 3-chloro-5-trifluoromethyl-2-pyridyl | |
| 1.259 | CH₃ | CH₃ | H | 3-chloro-5-nitro-2-pyridyl | |
| 1.260 | CH₃ | CH₂CH₃ | H | 3-chloro-5-nitro-2-pyridyl | |
| 1.261 | Cl | CH₂CH₃ | CH₃ | 3-chloro-5-nitro-2-pyridyl | |
| 1.262 | Br | CH₂CH₃ | CH₃ | 3-chloro-5-nitro-2-pyridyl | |
| 1.263 | CH₃ | CH₃ | H | 5-chloro-3-trifluoromethyl-2-pyridyl | |
| 1.264 | CH₃ | CH₂CH₃ | H | 5-chloro-3-trifluoromethyl-2-pyridyl | |
| 1.265 | Cl | CH₂CH₃ | CH₃ | 5-chloro-3-trifluoromethyl-2-pyridyl | |
| 1.266 | Br | CH₂CH₃ | CH₃ | 5-chloro-3-trifluoromethyl-2-pyridyl | |
| 1.267 | CH₃ | CH₂CH₃ | H | 3-chloro-2-cyanophenyl | 136-139 |
| 1.268 | CH₃ | CH₂CH₃ | H | 3-chloro-4-nitrophenyl | 102-103 |
| 1.269 | CH₃ | CH₂CH₃ | H | 2,6-dibromo-4-nitrophenyl | 205-207 |

TABLE 2

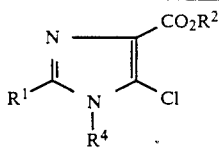

| No. | R¹ | R² | R⁴ | mp (°C.) |
|---|---|---|---|---|
| 2.001 | CH₃ | CH₂CH₃ | 2,4-dinitrophenyl | 181-182 |
| 2.002 | CCl₃ | CH₂CH₃ | 2,4-dinitrophenyl | 149-151 |
| 2.003 | CH₃ | CH₂CH₃ | 2,4-dichlorophenyl | |
| 2.004 | CCl₃ | CH₂CH₃ | 2,4-dichlorophenyl | |
| 2.005 | CH₃ | CH₂CH₃ | 2,4-dibromophenyl | |
| 2.006 | CCl₃ | CH₂CH₃ | 2,4-dibromophenyl | |
| 2.007 | CH₃ | CH₂CH₃ | 2,4,6-trichlorophenyl | |
| 2.008 | CCl₃ | CH₂CH₃ | 2,4,6-trichlorophenyl | |
| 2.009 | CH₃ | CH₂CH₃ | 2,4-dicyanophenyl | |
| 2.010 | CCl₃ | CH₂CH₃ | 2,4-dicyanophenyl | |

TABLE 2-continued

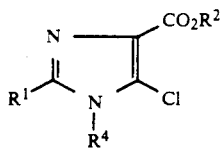

| No. | $R^1$ | $R^2$ | $R^4$ | mp (°C.) |
|---|---|---|---|---|
| 2.011 | $CH_3$ | $CH_2CH_3$ | 4-chloro-2-nitrophenyl | |
| 2.012 | $CCl_3$ | $CH_2CH_3$ | 4-chloro-2-nitrophenyl | |
| 2.013 | $CH_3$ | $CH_2CH_3$ | 4-chloro-2-fluorophenyl | |
| 2.014 | $CCl_3$ | $CH_2CH_3$ | 4-chloro-2-fluorophenyl | |
| 2.015 | $CH_3$ | $CH_2CH_3$ | 4-chloro-2-cyanophenyl | |
| 2.016 | $CCl_3$ | $CH_2CH_3$ | 4-chloro-2-cyanophenyl | |
| 2.017 | $CH_3$ | $CH_2CH_3$ | 4-chloro-2-trifluoromethylphenyl | |
| 2.018 | $CCl_3$ | $CH_2CH_3$ | 4-chloro-2-trifluoromethylphenyl | |
| 2.019 | $CH_3$ | $CH_2CH_3$ | 4-bromo-2-nitrophenyl | |
| 2.020 | $CCl_3$ | $CH_2CH_3$ | 4-bromo-2-nitrophenyl | |
| 2.021 | $CH_3$ | $CH_2CH_3$ | 4-bromo-2-chlorophenyl | |
| 2.022 | $CCl_3$ | $CH_2CH_3$ | 4-bromo-2-chlorophenyl | |
| 2.023 | $CH_3$ | $CH_2CH_3$ | 4-bromo-2-fluorophenyl | |
| 2.024 | $CCl_3$ | $CH_2CH_3$ | 4-bromo-2-fluorophenyl | |
| 2.025 | $CH_3$ | $CH_2CH_3$ | 4-bromo-2-cyanophenyl | |
| 2.026 | $CCl_3$ | $CH_2CH_3$ | 4-bromo-2-cyanophenyl | |
| 2.027 | $CH_3$ | $CH_2CH_3$ | 4-bromo-2-trifluoromethylphenyl | |
| 2.028 | $CCl_3$ | $CH_2CH_3$ | 4-bromo-2-trifluoromethylphenyl | |
| 2.029 | $CH_3$ | $CH_2CH_3$ | 4-cyano-2-chlorophenyl | |
| 2.030 | $CCl_3$ | $CH_2CH_3$ | 4-cyano-2-chlorophenyl | |
| 2.031 | $CH_3$ | $CH_2CH_3$ | 4-cyano-2-fluorophenyl | |
| 2.032 | $CCl_3$ | $CH_2CH_3$ | 4-cyano-2-fluorophenyl | |
| 2.033 | $CH_3$ | $CH_2CH_3$ | 4-cyano-2-nitrophenyl | |
| 2.034 | $CCl_3$ | $CH_2CH_3$ | 4-cyano-2-nitrophenyl | |
| 2.035 | $CH_3$ | $CH_2CH_3$ | 4-cyano-2-bromophenyl | |
| 2.036 | $CCl_3$ | $CH_2CH_3$ | 4-cyano-2-bromophenyl | |
| 2.037 | $CH_3$ | $CH_2CH_3$ | 4-cyano-2-trifluoromethylphenyl | |
| 2.038 | $CCl_3$ | $CH_2CH_3$ | 4-cyano-2-trifluoromethylphenyl | |
| 2.039 | $CH_3$ | $CH_2CH_3$ | 4-nitro-2-chlorophenyl | 119–120 |
| 2.040 | $CCl_3$ | $CH_2CH_3$ | 4-nitro-2-chlorophenyl | 157–158 |
| 2.041 | $CH_3$ | $CH_2CH_3$ | 4-nitro-2-bromophenyl | |
| 2.042 | $CCl_3$ | $CH_2CH_3$ | 4-nitro-2-bromophenyl | |
| 2.043 | $CH_3$ | $CH_2CH_3$ | 4-nitro-2-cyanophenyl | |
| 2.044 | $CCl_3$ | $CH_2CH_3$ | 4-nitro-2-cyanophenyl | |
| 2.045 | $CH_3$ | $CH_2CH_3$ | 4-trifluoromethyl-2-chlorophenyl | |
| 2.046 | $CCl_3$ | $CH_2CH_3$ | 4-trifluoromethyl-2-chlorophenyl | |
| 2.047 | $CH_3$ | $CH_2CH_3$ | 4-trifluoromethyl-2-bromophenyl | |
| 2.048 | $CCl_3$ | $CH_2CH_3$ | 4-trifluoromethyl-2-bromophenyl | |
| 2.049 | $CH_3$ | $CH_2CH_3$ | 4-trifluoromethyl-2-cyanophenyl | |
| 2.050 | $CCl_3$ | $CH_2CH_3$ | 4-trifluoromethyl-2-cyanophenyl | |
| 2.051 | $CH_3$ | $CH_2CH_3$ | 2,6-dichloro-4-trifluoromethylphenyl | |
| 2.052 | $CCl_3$ | $CH_2CH_3$ | 2,6-dichloro-4-trifluoromethylphenyl | |
| 2.053 | $CH_3$ | $CH_2CH_3$ | 2,6-dinitro-4-trifluoromethylphenyl | |
| 2.054 | $CCl_3$ | $CH_2CH_3$ | 2,6-dinitro-4-trifluoromethylphenyl | |
| 2.055 | $CH_3$ | $CH_2CH_3$ | 2,4-dinitro-6-cyanophenol | |
| 2.056 | $CCl_3$ | $CH_2CH_3$ | 2,4-dinitro-6-cyanophenol | |
| 2.057 | $CH_3$ | $CH_2CH_3$ | 2,4-dinitro-6-trifluoromethylphenyl | |
| 2.058 | $CCl_3$ | $CH_2CH_3$ | 2,4-dinitro-6-trifluoromethylphenyl | |
| 2.059 | $CH_3$ | $CH_2CH_3$ | 2,4-dinitro-6-carbethoxyphenyl | |
| 2.060 | $CCl_3$ | $CH_2CH_3$ | 2,4-dinitro-6-carbethoxyphenyl | |
| 2.061 | $CH_3$ | $CH_2CH_3$ | 2-nitro-4-carbethoxyphenyl | |
| 2.062 | $CCl_3$ | $CH_2CH_3$ | 2-nitro-4-carbethoxyphenyl | |
| 2.063 | $CH_3$ | $CH_2CH_3$ | 2,6-dichloro-4-nitrophenyl | |
| 2.064 | $CCl_3$ | $CH_2CH_3$ | 2,6-dichloro-4-nitrophenyl | 185–187 |

USE EXAMPLE

The influence of various representatives of the herbicidal agents, or combinations of agent and antidote, according to the invention on the growth of unwanted and crop plants compared with that of the herbicidal active ingredient alone is demonstrated in the following greenhouse experiments.

The vessels employed were plastic flowerpots having a volume of 300 cm³ and filled with a sandy loam containing about 3.0% humus. The seeds of the test plants were sown separately, according to species, and the soil was moistened. Transparent plastic covers were then placed on the vessels to ensure uniform germination and plant growth.

For the postemergence treatment, the plants were grown, depending on growth form, to a height of 3 to 15 cm before being treated with the active ingredients, which were suspended or emulsified in water and sprayed through finely distributing nozzles.

In the biological experiments, compound V.2 was used as cyclohexenone derivative V:

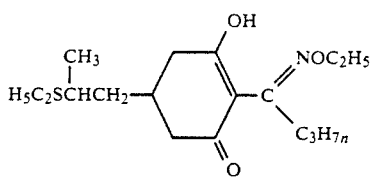

The formulations contain from 0.1 to 95, and preferably 0.5 to 90, % by weight of active ingredient and safener. The amounts of herbicidal active ingredient applied range from 0.001 to 0.5 kg/ha.

The herbicidal active ingredient V.2 was used (on its own and together with the safener) in the spray liquor as a commercially formulated product (184 g/l EC) together with the same amounts of solvent system XXII given in the table for the safener.

All the safeners were formulated in a mixture consisting of 80% of cyclohexenones and 20% of Emulphor EL (formulation XXII) with 10 wt % of active ingredient.

The vessels were set up in the greenhouse-heat-loving species at from 18° to 35° C., and those from more moderate climates at from 10° to 25° C.

The experiment was run for from 3 to 5 weeks. During this period, the plants were tended and their reaction to the various treatments was assessed. Damage caused by the chemical agents was evaluated on a 0 to 100 scale, compared with untreated control plants. 0 denotes no damage, and 100 denotes complete destruction (Triticum aestivum, wheat).

The table below demonstrates the safening action of compounds nos. 1.038 and 1.039; the tolerance of the cyclohexenone derivative V.2 by the crop plant was improved considerably.

TABLE A

Reduction in the damage caused by the herbicide V.2 to wheat as a result of combination with compounds 1.038 and 1.039 according to the invention

| App. rate Herbicidal act. ingr. | | Safener | | Damage to wheat |
|---|---|---|---|---|
| No. | [kg/ha] | No. | [kg/ha] | in % |
| V.2 | 0.015 | — | | 44 |
| | 0.03 | — | | 80 |
| V.2 | 0.015 | 1.038 | 0.06 | 0 |
| | 0.03 | | 0.125 | 20 |
| V.2 | 0.015 | 1.039 | 0.06 | 0 |
| | 0.03 | | 0.125 | 10 |

We claim:

1. A compound selected from the compounds of the formulae Ia and Ib

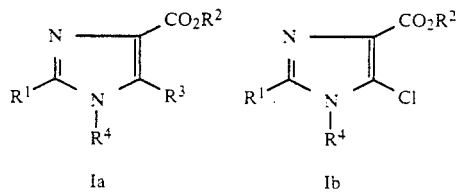

where
R$^1$ is halogen or C$_1$-C$_4$-alkyl which may bear from one to three chlorine atoms,
R$^2$ is C$_1$-C$_6$-alkyl which may bear from one to three of the radicals halogen, C$_1$-C$_4$-alkoxy and/or C$_1$-C$_4$-alkoxy-C$_1$-C$_4$-alkoxy, or is C$_3$-C$_6$-alkenyl, C$_3$-C$_6$-alkynyl or C$_3$-C$_6$-cycloalkyl,
R$^3$ is hydrogen or C$_1$-C$_4$-alkyl,
R$^4$ is a phenyl ring or a 5- or 6- membered heteroaromatic ring selected from the group consisting of pyrrole, pyrazole, imidazole, furan, thiophene, oxazole, thiazole, isoxazole, isothiazole, pyridine, pyridazine, pyrimidine or pyrazine, and these aromatic rings may bear from one to three of the following groups: halogen, C$_1$-C$_4$-alkyl, C$_1$-C$_4$-haloalkyl, C$_1$-C$_4$-alkoxy, C$_1$-C$_4$-haloalkoxy, C$_1$-C$_4$-alkylthio, C$_1$-C$_4$-alkylsulfinyl, C$_1$-C$_4$-alkylsulfonyl, C$_1$-C$_4$-alkylcarbonyl, C$_1$-C$_4$-alkoxycarbonyl, carboxyl, nitro and/or cyano.

2. The compound of claim 1, of the formula Ia, wherein R$^1$ is CH$_3$, R$^2$ is CH$_2$CH$_3$, R$^3$ is H and R$^4$ is 2,4-dichlorophenyl.

* * * * *

UNITED STATES PATENT AND TRADEMARK OFFICE
CERTIFICATE OF CORRECTION

PATENT NO. : 5,043,454

DATED : August 27, 1991

INVENTOR(S) : Ulrich WRIEDE et al.

It is certified that error appears in the above-identified patent and that said Letters Patent is hereby corrected as shown below:

On the Cover Sheet:

Please insert the following:
-- [30]   Foreign Application Priority Data
      January 27, 1989 [DE]  Fed. Rep. of Germany ..... 3902439--

Signed and Sealed this

Twenty-ninth Day of November, 1994

Attest:

BRUCE LEHMAN

Attesting Officer

Commissioner of Patents and Trademarks